(12) United States Patent
Tang

(10) Patent No.: US 9,806,536 B2
(45) Date of Patent: Oct. 31, 2017

(54) METHOD AND APPARATUS FOR WIRELESS MAGNETIC POWER TRANSMISSION

(71) Applicant: Sai Chun Tang, Boston, MA (US)

(72) Inventor: Sai Chun Tang, Auburnbdale, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 379 days.

(21) Appl. No.: 14/432,330

(22) PCT Filed: Oct. 11, 2013

(86) PCT No.: PCT/US2013/064574
§ 371 (c)(1),
(2) Date: Mar. 30, 2015

(87) PCT Pub. No.: WO2014/059294
PCT Pub. Date: Apr. 17, 2014

(65) Prior Publication Data
US 2015/0244178 A1    Aug. 27, 2015

Related U.S. Application Data

(60) Provisional application No. 61/713,209, filed on Oct. 12, 2012.

(51) Int. Cl.
*H02J 5/00* (2016.01)
*A61N 1/378* (2006.01)
(Continued)

(52) U.S. Cl.
CPC .......... *H02J 5/005* (2013.01); *A61B 1/00029* (2013.01); *A61B 5/026* (2013.01);
(Continued)

(58) Field of Classification Search
CPC .................. H02J 5/005; H02J 7/025
(Continued)

(56) References Cited

U.S. PATENT DOCUMENTS 8,471,410 B2 *   6/2013   Karalis .................. B60L 3/0069
                                                              307/104
2006/0158190 A1 *   7/2006   Saylor .............. G01R 33/34046
                                                              324/318
(Continued)

OTHER PUBLICATIONS

International Search Report and Written Opinion under date of mailing of Feb. 13, 2014, in connection with PCT/US2013/064574.

*Primary Examiner* — Joseph Chang
(74) *Attorney, Agent, or Firm* — Quarles & Brady LLP

(57) ABSTRACT

Systems for wirelessly transmitting power to an implanted medical device. The wireless transmission system including a first and second transmitting coil both the first and second coil having substantially equal diameters and at least one conductor winding. A gap between the first transmitting second transmitting coil extending along a common axis by a distance equal to the radius of the first transmitting coil. A plurality of capacitors connected in series along the at least one conductor of the transmitting coils to divide the transmitting coils into a plurality of coil segments. An input connection is electronically coupled to the transmitting coils to deliver an excitation voltage to the transmitting coils to produce a substantially uniform magnetic field between the first transmitting coil and the second transmitting coil.

17 Claims, 7 Drawing Sheets

(51) Int. Cl.
  *A61N 1/372* (2006.01)
  *H01F 38/14* (2006.01)
  *H02J 7/02* (2016.01)
  *A61B 1/00* (2006.01)
  *A61B 5/026* (2006.01)

(52) U.S. Cl.
  CPC ....... *A61N 1/3787* (2013.01); *A61N 1/37223* (2013.01); *H01F 38/14* (2013.01); *H02J 7/025* (2013.01); *A61B 2560/0219* (2013.01)

(58) Field of Classification Search
  USPC .......................................................... 307/104
  See application file for complete search history.

(56) References Cited

U.S. PATENT DOCUMENTS

| | | |
|---|---|---|
| 2011/0193418 A1 | 8/2011 | Hennig et al. |
| 2012/0038219 A1* | 2/2012 | Wang ................... H04B 5/0037 307/104 |
| 2012/0095744 A1 | 4/2012 | Rahman et al. |
| 2012/0119700 A1 | 5/2012 | Forsell |
| 2012/0153739 A1* | 6/2012 | Cooper ................... H02J 7/025 307/104 |

* cited by examiner

METHOD AND APPARATUS FOR WIRELESS MAGNETIC POWER TRANSMISSION

CROSS-REFERENCE TO RELATED APPLICATIONS

This application represents the national stage entry of PCT International Patent Application PCT/US2013/064574 filed Oct. 11, 2013, which claims priority to U.S. Provisional Application Ser. No. 61/713,209, filed Oct. 12, 2012, the disclosures of both of the above-mentioned applications are incorporated herein by reference for all purposes.

STATEMENT REGARDING FEDERALLY SPONSORED RESEARCH OR DEVELOPMENT

Not applicable.

BACKGROUND OF THE INVENTION

The subject matter disclosed herein relates generally to medical devices, and, more particularly, to a system and method for providing wireless power transmission to implantable electronic medical devices.

Implantable electronic medical devices, such as capsule endoscopes, cardiac implants, and blood-flow monitors have long been used in the medical profession for both diagnosis and treatment purposes. As these devices advance in both complexity and capability, they require more power to operate. Due to the location of these devices inside the human body, providing the required power has been difficult using existing methods.

Capsule endoscopy utilizes camera and lighting elements placed in a form factor suitable for a patient to swallow. The progression of the capsule endoscope through the patients gastrointestinal (GI) tract allows the capsule endoscope to capture images of the patients' GI tract. This examination of the GI tract allows physicians to examine and/or discover gastrointestinal bleeding, tumors of the small intestine, polyps, and Crohn's disease. Capsule endoscopy is beneficial as it is less invasive than traditional endoscopy for the patient, and allows for images to be captured of the small intestine which can be difficult with traditional endoscopy.

However, the viability of capsule endoscopy is limited by the power limitations inherent in the miniaturized devises. Currently, capsule endoscopes are battery powered and are typically limited to approximately eight hours of operating time. As the capsule endoscopes pass through the GI tract naturally via the patients peristaltic contractions, the capsule endoscope may not pass through the area of the GI tract of interest to the physician prior to the battery power being exhausted.

Other implanted medical devices including cardiac implants such as pacemakers and artificial hearts have additional issues associated with ensuring these devices have sufficient power. Currently, these cardiac devices rely on embedded batteries which can require surgery for battery replacement. Surgery, even routine, carries with it an inherent risk to the patient. In addition to this inherent risk, surgery is both uncomfortable and expensive for the patient.

To help address this issue, modern artificial hearts and pacemakers may contain rechargeable batteries that can be recharged using magnetic coupling. However, current magnetic coupling techniques require the charging circuit implanted in the body to be close to the surface of the skin. In the cases of cardiac implants, this can require lengths of wire to be placed close to the skin, sometimes within 1 cm, that are then connected to the implanted cardiac device. These wires are susceptible to reliability issues due to the dynamic nature of the human body which can cause the wires to frequently move, possibly leading to the wires being damaged or disconnected from the implanted device, which may required surgery to repair. Additionally, patients that have these wires implanted cannot undergo MRI scans due to the risk of RF heating causing injury to the patient.

Implantable blood flow monitors have similar limitations. Implantable blood flow monitors can either contain batteries having a finite amount of power or use transcutaneous transformers to wirelessly charge the devices. As with the cardiac implants, if the device is not located close to the surface of the skin, within approximately 1 cm, wires may need to be run from the device to the surface of the skin to allow for charging. This can lead reliability issues due to the movement of the wires along with the body, possibly leading to the wires being damaged or disconnected from the implanted device. Batteries, while replaceable, require additional surgery and can be prohibitively expensive for the patient.

While current technology does exist to wirelessly charge medical devices, it is limited in both its reliability and capability. As previously stated, current wireless power transmission systems may require the device, or the charging circuit, to be located close to the surface of the skin, typically within 1 cm. Additionally, the current designs of these transcutaneous transformer devices are very sensitive to the alignment of the transmission coil to the receiving coil. Precise coil alignment is needed to achieve maximum energy transfer. Improper alignment significantly reduces the power transfer. Finally, the small separation distance required between the transmission and receiving coils, combined with the requirement of coil alignment, means that current technology is not applicable to an ambulatory and deeply embedded device such as a capsule endoscope.

Modern wireless magnetic charging is further limited by the size of the transmission coil. A typical transmission coil for an artificial heart may be approximately 90 mm in diameter. While a 90 mm coil can transmit sufficient energy to charge an artificial heart, it requires that the receiving coil be located close to the skin surface, within approximately 1 cm, to ensure proper power transmission. To adequately transmit power deep into the body, where the device itself is located, requires approximately a 300 mm transmission coil. A coil of this size is capable of generating a uniform magnetic field deep within the body to charge the device without the requirement of wires run to near the surface of the skin. However, this is prohibitive as a coil of this size requires an extremely high voltage source in order to generate the required electrical current though the transmission coil due to the inductive impedance associated with a coil of the size described above. As an example, to provide a minimum 300 mW of power to operate a capsule endoscope located deep in the patients body, the required operating voltage of the coil may be as high as 3.5 kV. For powering an artificial heart requiring 10 W of power, the voltage would be many times higher. Due to the sensitivity of surrounding medical equipment and safety concerns for the patients and medical personnel, as well as high manufacturing and operating costs, the current solutions for wirelessly transmitting power to an implanted medical device are not feasible.

Thus, it can be seen that there is a need for the current invention, which can allow for charging medical devices located deep within the body without requiring high operational voltages to achieve the required power transfer.

BRIEF DESCRIPTION OF THE INVENTION

The present embodiments overcome the aforementioned problems by providing a magnetic power transmission device that can wirelessly provide power to implanted devices deep in a human body without requiring the internal implanted power device, nor a separate charging circuit, to be located near the surface of the skin. Additionally, the following embodiments do not require high operational voltages to create the required uniform magnetic field deep in the body.

Accordingly, embodiments of the present invention include a system for wirelessly transferring energy to an implanted medical device. The system comprises a wireless power transmitting device, the wireless power transmitting device includes a first transmitting coil having at least one conductor winding, a first radius and a first diameter, and a second transmitting coil, the second transmitting coil having at least one conductor winding, a second radius and a second diameter. The first and second transmitting coil are arranged to extend along a common axis with the first transmitting coil, wherein the first diameter and the second diameter are substantially equal. A gap is arranged between the first transmitting coil and the second transmitting coil and extending along a common axis to a distance equal to the first radius of the first transmitting coil. A first plurality of capacitors are connected in series along the at least one conductor winding of the first transmitting coil to divide the coil conductor winding into a first plurality of coil segments. A second plurality of capacitors are connected in series along the at least one conductor winding of the second transmitting coil to divide the coil conductor winding into a second plurality of coil segments. Finally, an input connection is electrically coupled to the first transmitting coil and the second transmitting coil to deliver an excitation voltage to the first transmitting coil and the second transmitting coil that is substantially equal to a theoretical excitation voltage required to produce a substantially uniform magnetic field between the first transmitting coil and the second transmitting coil divided by a sum of the first plurality of coil segments and the second plurality of coil segments.

A system for wirelessly transferring energy to an implanted medical device. The system comprises a wireless power transmitting device, the wireless power transmitting device includes a first transmitting coil having at least one conductor winding, a first radius and a first diameter, and a second transmitting coil, the second transmitting coil having at least one conductor winding, a second radius and a second diameter. The first and second transmitting coil are arranged to extend along a common axis with the first transmitting coil, wherein the first diameter and the second diameter are substantially equal. A gap is arranged between the first transmitting coil and the second transmitting coil and extending along a common axis to a distance equal to the first radius of the first transmitting coil. A first plurality of capacitors are connected in series along the at least one conductor winding of the first transmitting coil to divide the coil conductor winding into a first plurality of coil segments. A second plurality of capacitors are connected in series along the at least one conductor winding of the second transmitting coil to divide the coil conductor winding into a second plurality of coil segments. A power source is electrically coupled to the first transmitting coil and the second transmitting coil and configured to deliver an excitation voltage to the first transmitting coil and the second transmitting coil substantially equal to a theoretical excitation voltage required to produce a substantially uniform magnetic field between the first transmitting coil and the second transmitting coil divided by a sum of the first plurality of coil segments and the second plurality of coil segments.

A system for wirelessly transferring energy to an implanted medical device. The system comprises a wireless power transmitting device, the wireless power transmitting device includes a first transmitting coil having at least one conductor winding, and a second transmitting coil, the second transmitting coil having at least one conductor winding. The first transmitting coil and the second transmitting coil being substantially equal in diameter. The first and second transmitting coil are located parallel to each other and separated co-axially by a distance equal to a radius of the first transmitting coil. wherein the first diameter and the second diameter are substantially equal. The first transmitting coil conductor winding and the second transmitting coil conductor winding include a plurality of capacitors connected in series, wherein the series capacitors are installed along the first transmitting coil conductor winding and the second transmitting coil conductor winding to divide the coil conductor winding into a plurality of coil segments. The first transmitting coil and the second transmitting coil having a resonant frequency based on an operating frequency of the wireless power transmitting device. The wireless power transmitting device is configured to produce a uniform magnetic field between the first transmitting coil and the second transmitting coil when an excitation voltage is applied to the wireless power transmitting device. The system further comprises a wireless power receiving device, the wireless power receiving device including a receiving coil and a plurality of capacitors. The wireless power receiving device having a resonant frequency equal to the operating frequency of the wireless power transmitting device, wherein the wireless power receiving device is configured to convert the magnetic field generated by the wireless power transmitting device into electrical power.

In accordance with another embodiment of the invention, the above system for wirelessly transmitting energy to an implanted medical device may also include a wireless power receiving device, the wireless power receiving devices includes a receiving coil and a plurality of capacitors. The wireless power receiving device has a resonant frequency equal to the operating frequency of the wireless power transmitting device. Finally the wireless power receiving device is configured to convert the magnetic field generated by the wireless power transmitting device into electrical power.

To the accomplishment of the foregoing and related ends, the embodiments, then, comprise the features hereinafter fully described. The following description and the annexed drawings set forth in detail certain illustrative aspects of the invention. However, these aspects are indicative of but a few of the various ways in which the principles of the invention can be employed. Other aspects, advantages and novel features of the invention will become apparent from the following detailed description of the invention when considered in conjunction with the drawings.

BRIEF DESCRIPTION OF THE DRAWINGS

The embodiments will hereafter be described with reference to the accompanying drawings, wherein like reference numerals denote like elements, and.

DETAILED DESCRIPTION OF THE INVENTION

The various embodiments of the invention will be described in connection with a system or method for wireless magnetic charging of medical devices implanted in a human body. That is because the features and advantages of the invention are well suited for this purpose. Still, it should be appreciated that the various aspects of the invention can be applied in other wireless magnetic charging applications, not necessarily related to medical devices implanted within a human.

Specifically, embodiments of the invention provide a wireless magnetic charging device that can provide a uniform magnetic field deep within a human body for charging implanted medical devices. The wireless magnetic charging device can contain a segmented coil that can reduce the required voltage needed to transfer the required power to the implanted devices.

Figure 1:
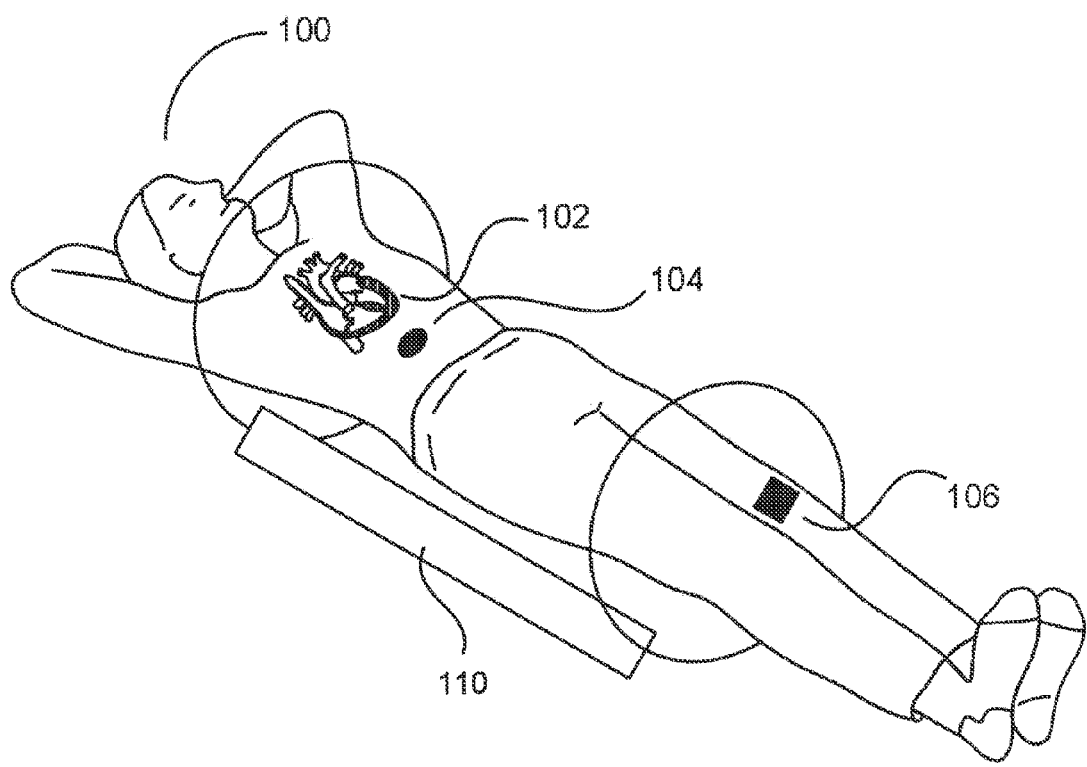
FIG. 1 is a perspective exploded view of a human body showing various implementations of implantable medical devices.

FIG. 1 shows a representation of a human body 100 showing a variety of implantable devices that serve as non-limiting examples of implantable medical devices that can be used with the present invention. For example, a cardiac implant 102 is shown in approximately the position it would be placed in a human patient. Also, an endoscopic capsule 104 can be located anywhere along the patients GI tract. Finally, a blood flow meter 106 is shown in the left leg of the human body 100. It should be noted that blood flow meter 106 can be located on different arteries in the body based on need and is only shown in the present location for illustrative purposes. These are but a few examples of implantable medical devices that can be used with the present invention. An exemplary depiction of a wireless charging system 110 is also shown to provide a representative example of a typical positioning of a wireless charging device when charging an implanted medical device, such as the cardiac implant 102, the endoscopic capsule 104, or the blood flow meter 106.

Figure 2:
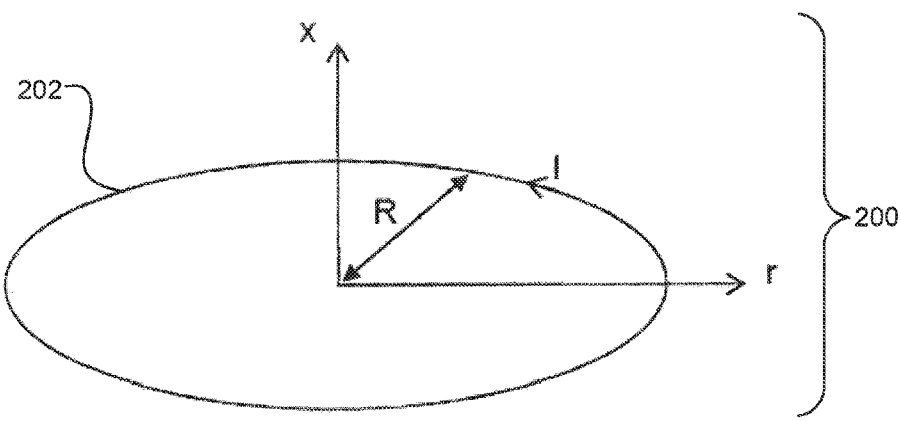
FIG. 2 is a representation view of a single transmission coil.

FIG. 2 shows an embodiment of a wireless transmission coil 200 using a single transmission coil 202 that could be used with the system 110 of FIG. 1. A single transmission coil setup may be used where the implanted medical device is not deep within the human body and where the location of the implanted medical device is sufficiently known such that the single transmission coil 202 can be positioned to ensure that the device is within a predetermined distance of the plane of the single transmission coil 202. Practically, the single transmission coil 202 can only provide a substantially uniform magnetic field approximately 3 cm from the plane of the single transmission coil 202. This can be insufficient to use for powering devices that are not fixed in a certain location such as a capsule endoscope or a endoscopic capsule robot due to the uniform magnetic field around the single transmission coil 202 being limited to approximately 3 cm.

Figure 3:
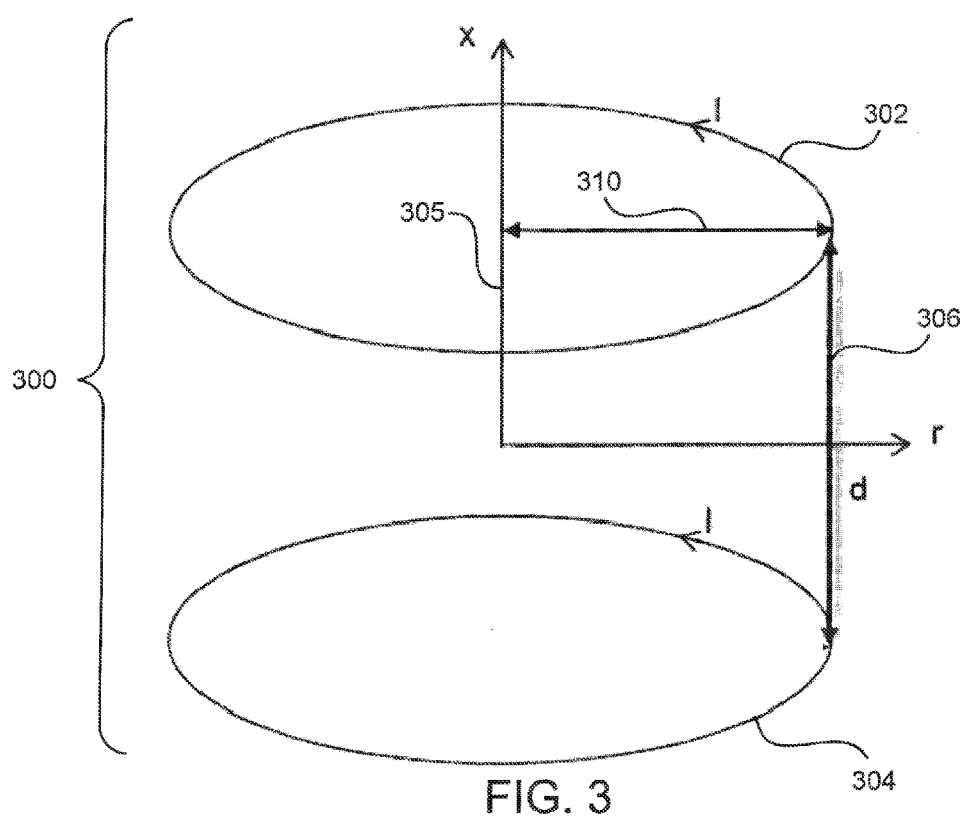
FIG. 3 is a representation view of multiple transmission coils.

FIG. 3 shows a wireless transmission coil 300 having a first transmission coil 302 and a second transmission coil 304 separated by a fixed distance 306. In one embodiment, the wireless magnetic transmission coil 300 can be a Helmholtz type coil. A Helmholtz coil can be used to provide an even magnetic field bounded by the two coils. In a Helmholtz coil, the first transmission coil 302 is located co-axially with, and parallel to, the second transmission coil 304. That is, the first transmission coil 302 and the second transmission coil 304 extend along a common axis 305. Additionally, the first transmission coil and the second transmission coil are separated by a distance substantially equal to the radius 310 of the transmission coil diameter in the axial direction, wherein the first transmission coil 302 has the substantially same diameter as the second transmission coil 304. To ensure maximum operational efficiency, the diameters of the two transmission coils should be substantially the same. Substantially equal is considered the two transmission coils having diameter differences of no more than, for example, ten percent.

Figure 4:
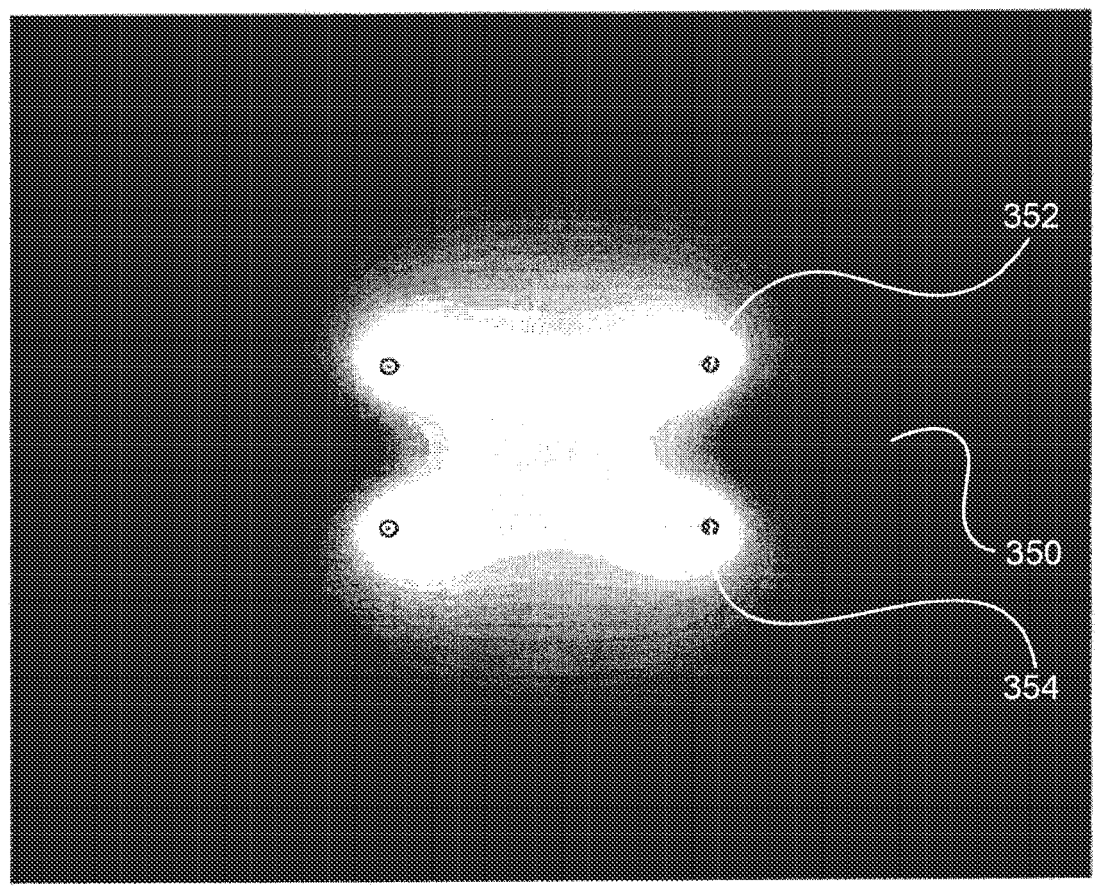
FIG. 4 is a FEA simulation showing the simulated magnetic field produced by two transmission coils configured as a Helmholtz coil.

FIG. 4 shows a simulated magnetic field 350 created by a Helmholtz coil arrangement. As can be seen in FIG. 4, the magnetic field is of a uniform strength between the first coil 352 and the second coil 354. Additionally, it should be noted the Helmholtz coil configuration is an exemplary configuration. Additional coil configurations can be used to achieve different results and can include modifying the number of coils, the coil diameters, the number of turns in each coils, or coil separation and inclination.

While a Helmholtz coil configuration can produce a uniform magnetic field between the first and second transmission coils, larger diameter transmission coils than are currently in use in the medical field are required to both produce a uniform magnetic field over a larger region of the body as well as to adequately transmit power to implants located deep in the human body. However, increasing the diameter of the transmission coils also increases the excitation voltage required to produce the required magnetic field. This is due to the proportional relationship between the inductive impedance in the transmission coil and the diameter of the transmission coil. Additionally, as the implanted devices require more power, additional conductor turns in the transmission coil may be required to create a magnetic field capable of transmitting the required amount of power to the implanted device. This increase in conductor turns can greatly increase the inductance of the transmission coil causing a significant increase in the impedance of the circuit. Additionally, due to the high frequencies required to ensure sufficient power transfer, the transmission coil impedance can increase even further. The resulting high impedance transmission coils can result in excitation voltages in the 1-5 kV range for low power devices such as capsule endoscopes, up to over 10 kV for high power devices such as artificial hearts. Excitation voltages at this level can be cost prohibitive due to the electric shielding and high-voltage insulation required to reduce the risk to persons as well as to other electronic equipment. Additionally, the infrastructure required to obtain the required excitation voltages may not be feasible.

Figure 5:
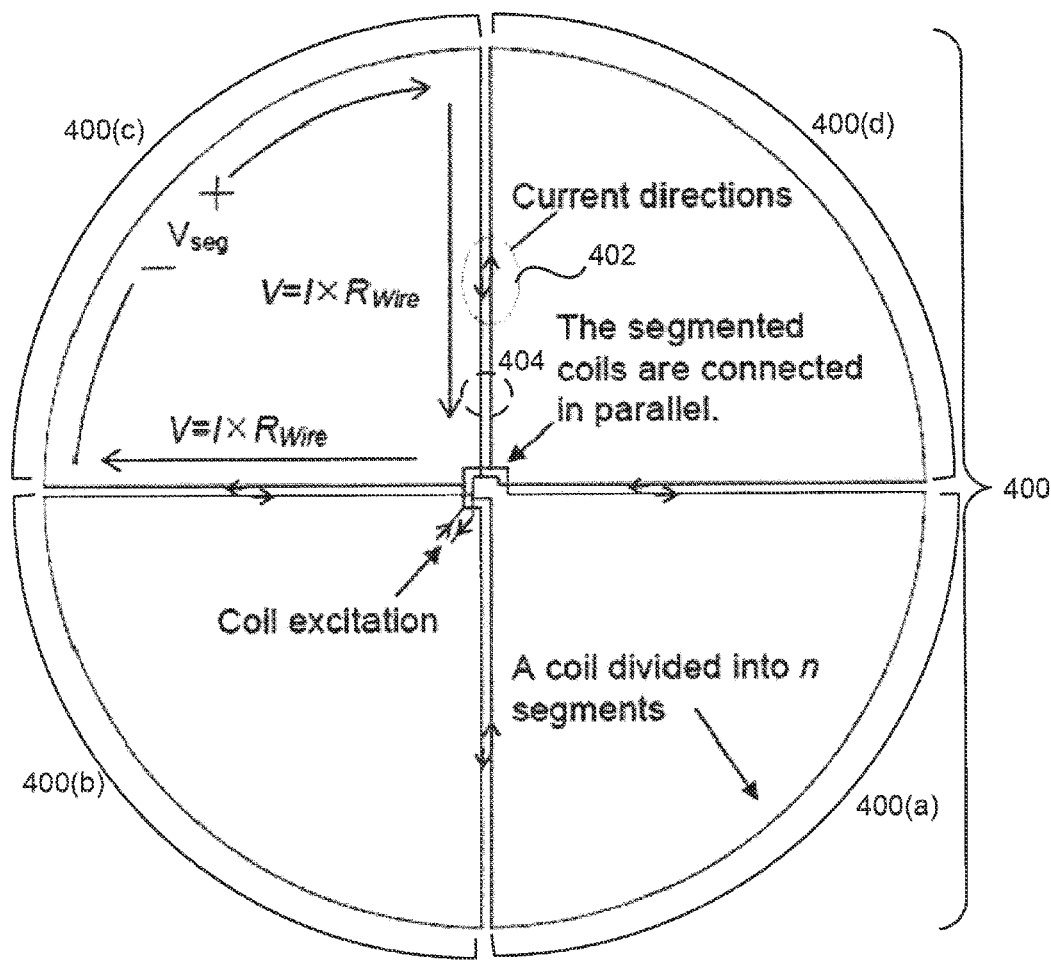
FIG. 5 is a schematic view of a transmission coil physically divided into four segments.

FIG. 5 demonstrates an embodiment for addressing the high impedance limitations associated with larger diameter and multi-turn transmission coils. In FIG. 5, the transmission coil 400 is segmented into a plurality of smaller, coil segments 400(a)-400(d) connected in a parallel configuration. The coil segments 400(a)-400(d) may be identical. The current 402 flow through each pair of wires 404 making up each coil segment can be in the opposite direction of the current flow 402 of the adjacent coil segment wires 404. This opposing current flow can effectively cancel out the opposing magnetic fields between coil segments. This cancellation of magnetic fields between coil segments can reduce the inductive impedance to a point less than that of the wire resistance itself, thus requiring a much lower excitation voltage requirement for each coil. In this embodiment, the required voltage for driving each smaller loop can be approximately equal the required excitation voltage for the whole coil divided by the number of coil segments.

While physical coil segmentation, as shown in FIG. 5, can significantly reduce the required excitation voltage, the increased connection points can increase conduction loss due to the additional wires needed for the multiple connections. For an alternative coil segmentation technique, we turn to FIG. 6.

Figure 6:
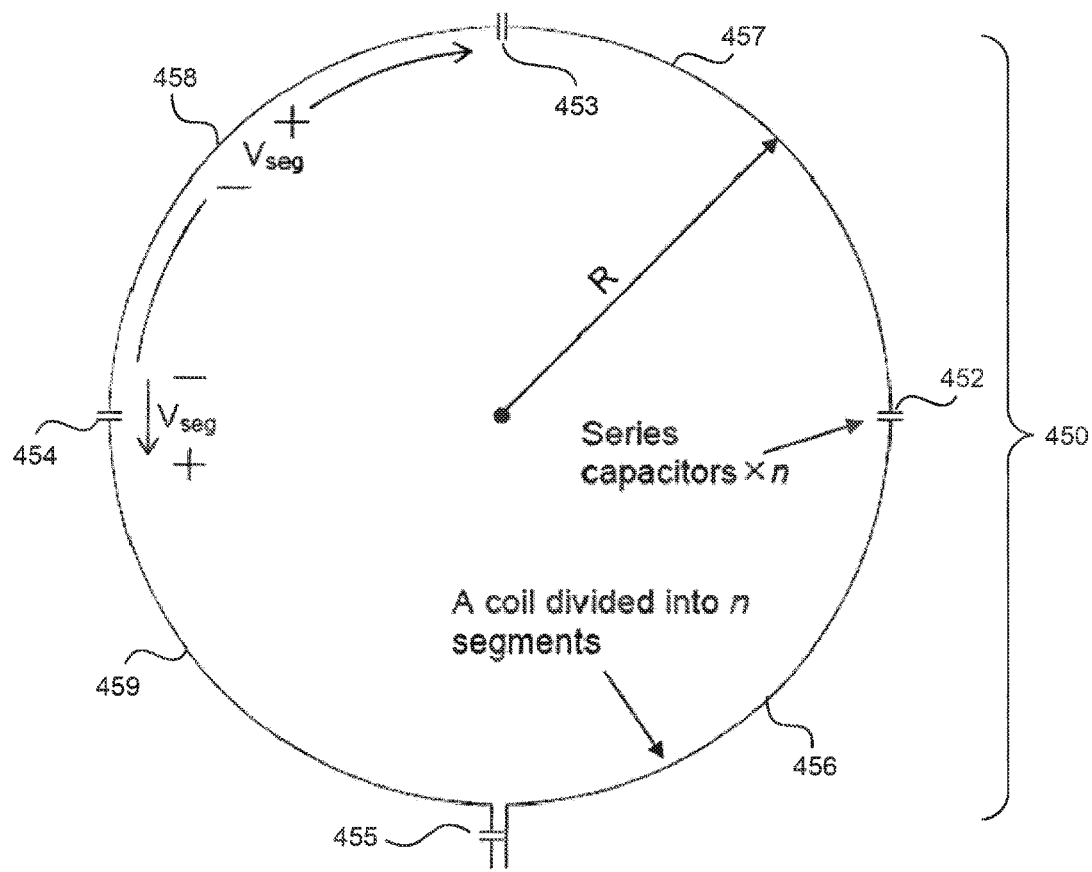
FIG. 6 is a schematic view of a transmission coil electrically divided into four segments.

FIG. 6 shows an exemplary embodiment for addressing the high impedance limitations associated with larger diameter and multi-turn transmission coils. A transmission coil 450 is divided into segments using series capacitors 452-455. The series capacitors 452-455 can be physically located along the length of the transmitting coil 450 to segment the transmitting coil 450 into a desired number of coil segments 456-459. The series capacitors 452-455 can be sized to provide a transmission coil 450 resonance frequency that is equal to the desired operating frequency of the wireless magnetic power transmission system. By placing the series capacitors 452-455 along the transmission coil 450, the voltage of each coil segment 456-459 can be substantially canceled out by the corresponding series capacitor 452-455 when the transmission coil 450 resonant frequency is equal to the system operating frequency as the voltage across each of the series capacitors 452-455 is equal and in opposite polarity to the voltage across the coil segments 456-459. Any residual voltage present on the coil segments 456-459 can be the result of the series resistance of the coil segment conductors. Additionally, this can result in the transmission coil segment 456-459 excitation voltage being equal to the total transmission coil 450 excitation voltage, divided by the total number of transmission coil segments 456-459. Furthermore, by operating the transmission coil 450 at the resonant frequency, the impedance of the coil can be minimized and can approximately equal the transmission coil 450 resistance. In a one design, the transmission coil 450 resistance would be less than five Ohms.

Figure 7:
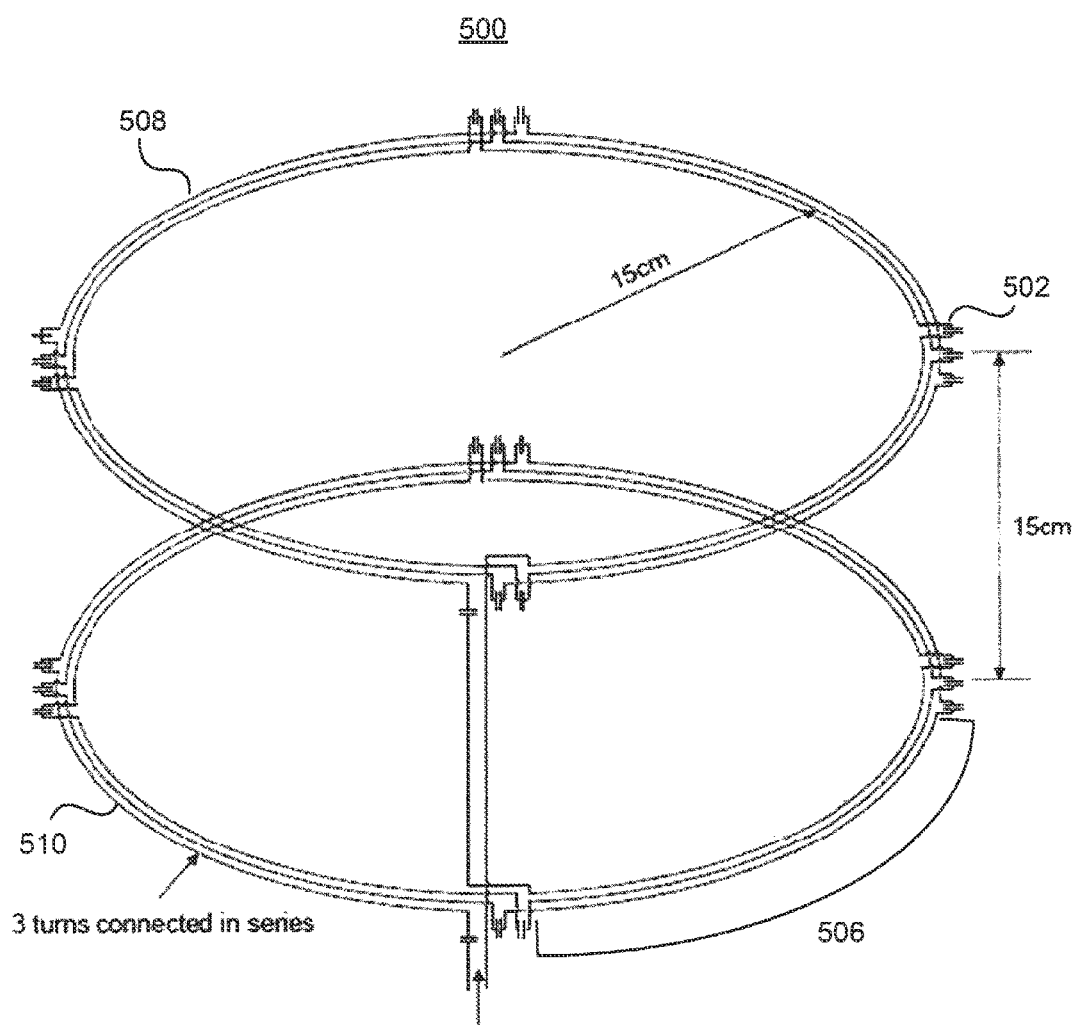
FIG. 7 is a perspective view of a segmented multi-turn, multi-coil transmission coil.

FIG. 7 shows a further embodiment wherein the transmission coil 500 is configured as a Helmholtz coil having two transmission coils 508 and 510 with each coil 508 and 510 having three turns. Each coil 508 and 510 is segmented by series capacitors 502 installed along the coil conductors. Each coil 508 and 510 is divided into twelve transition coil segments 506 for a total of twenty-four transmission coil segments 506. Thus, the excitation voltage for each segment is equal to the total transmission coil excitation voltage divided by twenty-four coil segments 506. In one exemplary configuration, the transmission coil segment 506 excitation voltage can be reduced to 7V or less. Furthermore, the capacitor values can be selected to provide a transmission coil 500 resonance frequency that is equal to a desired operating frequency of the wireless magnetic charging system. An operating frequency of the wireless magnetic charging system can be a frequency less than 15 MHz. Referring back to FIG. 3, it can be seen that the magnetic field in a Helmholtz coil is at its strongest and most uniform between the two coils 302 and 304. As such, in the preferred embodiment of FIG. 7, the patient should be positioned such that the implanted medical device is located between the first transmission coil 508 and the second transmission coil 510 to obtain the best power transfer.

In an exemplary embodiment, the desired operating frequency of the wireless magnetic power transmission system can be approximately 6.1 MHz. Once the operating frequency is known, the capacitance value can be determined using the formula for calculating resonance frequency, $$f = \frac{1}{2\pi\sqrt{L_{TX}C_{TX}}}$$

where $L_{TX}$ is the transmitting coil inductance and $C_{TX}$ is the required resultant capacitance of the series capacitors connecting to the coil segments. This can result in a required total series capacitance of 34.17 pF. Thus, where the coil is divided into twenty-four segments, as shown in FIG. 7, the value of each capacitor would be 34.17 pF multiplied by the number of transmission coil segments, resulting in each series capacitor being 820 pF.

Figure 8:
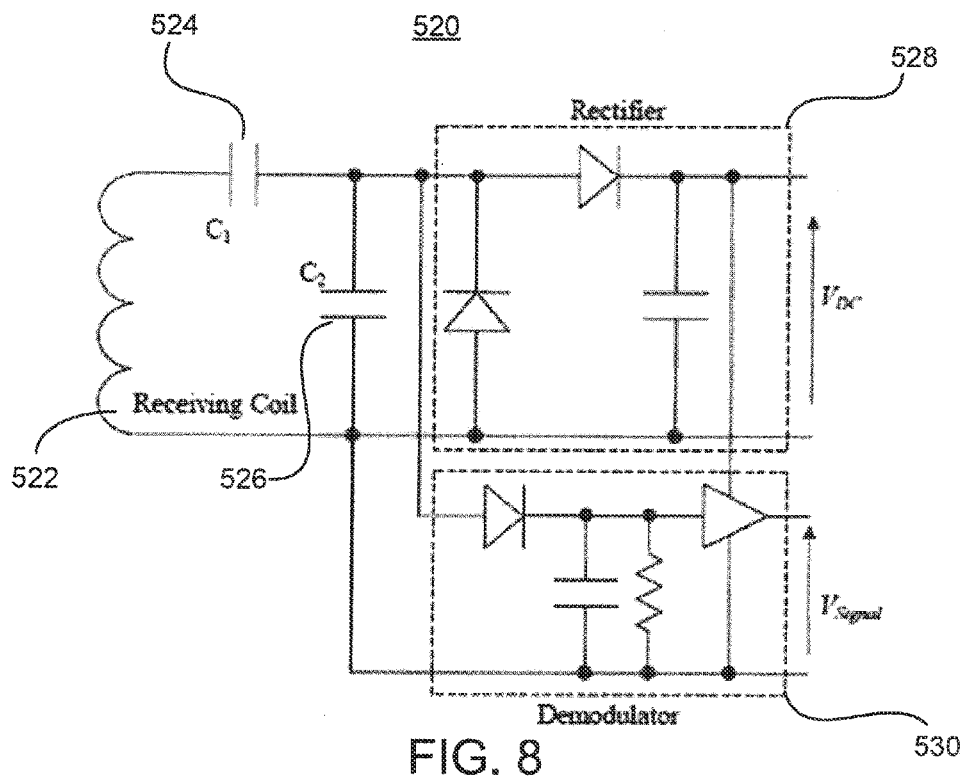
FIG. 8 is a schematic representation of a power receiving circuit.

FIG. 8 shows an exemplary embodiment of a power receiving circuit 520. The power receiving circuit 520 can be used to convert the magnetic energy generated by a wireless power transmission system into to electrical power. This power receiving circuit 520 can be integrated into an implanted medical device. In the preferred embodiment, the power receiving circuit 520 contains a receiving coil 522. The receiving coil 522 can be an air-core coil. In an exemplary embodiment, the air-core coil can be constructed of three turns of 26 AWG single strand enameled wire. An air-core coil can be advantageous due to the low cost and high power density. However, other receiving coil types, such as ferromagnetic core coils or other configurations of air-core coils can also be used. The power receiving circuit can also contain a plurality of capacitors. In a preferred embodiment, two capacitors 524 and 526 are placed across the receiving coil 522. Capacitors 524 and 526 can further be used to tune the resonant frequency of the power receiving circuit 520 to the operating frequency of the wireless magnetic power transmission system.

The power receiving circuit 520 can also contain a rectifier circuit 528. The rectifier circuit can rectify the high frequency AC power received by the receiving coil 522 into a DC voltage that can be utilized by an implanted medical device. The rectifier circuit can also be configured to regulate the output voltage. This can be accomplished using active or passive regulation techniques. The power receiving circuit can also contain a demodulation circuit 530. The demodulation circuit 530 can be used to extract any data signal content received by the power receiving circuit 520. Transmission of data signals is discussed in more detail below.

Figure 9:
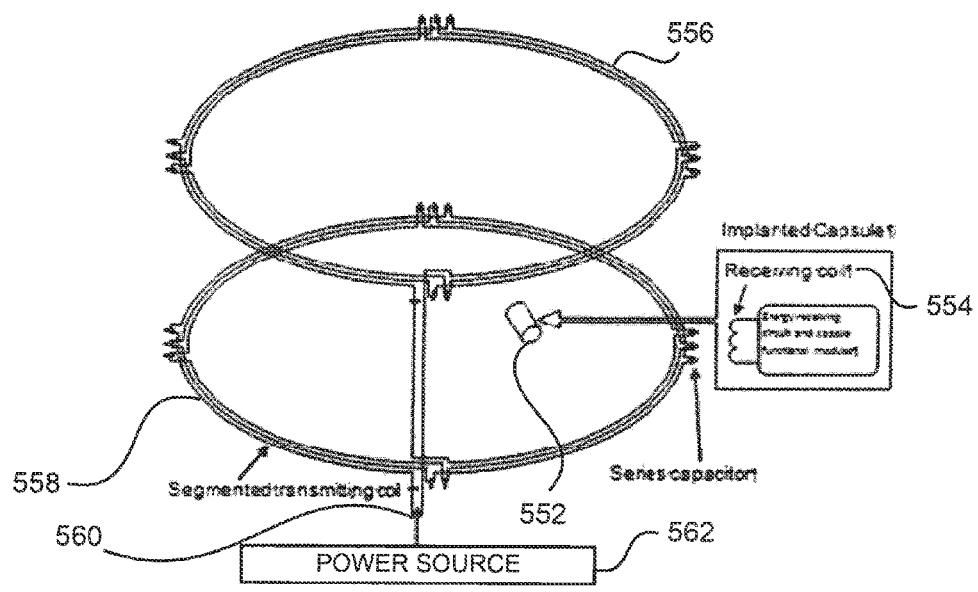
FIG. 9 is a perspective view of a multi-coil segmented power transmission coil showing the location of an implanted medical device that is to be charged.

FIG. 9 is an exemplary embodiment of an application of the present invention. A receiving coil 554 of a medical device 552 implanted in a human being is located in the space between two segmented transmission coils 556 and 558. Using the Helmholtz coil design discussed above, a uniform magnetic field is generated in the area between the two segmented transmission coils 556 and 558 when the required excitation voltage is applied to the transmission coils 556 and 558 through an input connection 560 by a power source 562. The excitation voltage, as explained above, can be substantially equal to a theoretical excitation voltage required to produce a substantially uniform magnetic field between the first transmitting coil and the second transmitting coil divided by a sum of the first plurality of coil segments and the second plurality of coil segments. In this case, "substantially" may refer, for example, to a reasonable margin of error such as 10 percent or more. The substantially uniform magnetic field generated by the transmission coils 556 and 558 can then be converted by the receiving coil into electrical power which can be supplied to the implanted medical device. The theoretical excitation voltage can be the voltage required to produce a calculated current, such as one ampere, through the transmission coils 556 and 558 to transfer a required amount of energy in the magnetic field. The theoretical excitation voltage can vary with variations in the impedance of the transmission coils 556 and 558.

While the embodiments and figures show a circular Helmholtz coil configuration, other coil configurations such as Maxwell coils could also be used. Furthermore, the transmitting coos are not limited to wrapping around the patients body as seen in the above embodiments. Some non-limiting examples of other coil orientations include one coil located on the front of the patient and another located behind the patient, one coil on the right side of the patient and one coil on the left side of the patient, and any combination thereof that produces the maximum power to the implant in any orientation.

Additionally, in other embodiments, a data signal can be transmitted for communicating with the implanted devices using the operating frequency for transmitting the power as the carrier frequency. In one embodiment, the data signal can be transmitted using on-off keying (OOK) modulation, but it is to be understood in the art that other signal transmission methodologies may also be employed. The data signal can be used for, but is not limited to, controlling a capsule endoscope.

In another embodiment, a navigation system can be used to trace the location of ambulatory implanted medical devices, such as capsule endoscopes, so that the position of the transmitting coil can be controlled, ensuring that the implantable device is always located around the midpoint between the centers of the two transmission coils to achieve maximum power transfer.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein.

The detailed description is to be read with reference to the figures. The figures depict selected embodiments and are not intended to limit the scope of embodiments of the invention. Skilled artisans will recognize the examples provided herein have many useful alternatives and fall within the scope of embodiments of the invention. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Embodiments of the invention may be described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., digital signal processing elements, logic elements, diodes, etc., which may carry out a variety of functions under the control of one or more processors or other control devices. Other embodiments may employ program code, or code in combination with other circuit components.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Finally, it is expressly contemplated that any of the processes or steps described herein may be combined, eliminated, or reordered. Accordingly, this description is meant to be taken only by way of example, and not to otherwise limit the scope of this invention.

I claim:

1. A system for wirelessly transferring energy to an implanted medical device, the system comprising:
   a wireless power transmitting device, the wireless power transmitting device including:
      a first transmitting coil having at least one conductor winding, a first radius and a first diameter;
      a second transmitting coil having at least one conductor winding, a second radius, and a second diameter and arranged to extend along a common axis with the first transmitting coil, wherein the first diameter and the second diameter are substantially equal;
      a gap arranged between the first transmitting coil and the second transmitting coil and extending along the common axis a distance equal to the first radius of the first transmitting coil;
      a first plurality of capacitors connected in series along the at least one conductor winding of the first transmitting coil to divide the coil conductor winding into a first plurality of coil segments;
      a second plurality of capacitors connected in series along the at least one conductor winding of the second transmitting coil to divide the coil conductor winding into a second plurality of coil segments; and
      an input connection electrically coupled to the first transmitting coil and the second transmitting coil to deliver an excitation voltage to the first transmitting coil and the second transmitting coil substantially equal to a theoretical excitation voltage required to produce a substantially uniform magnetic field between the first transmitting coil and the second transmitting coil divided by a sum of the first plurality of coil segments and the second plurality of coil segments.

2. The system of claim 1, wherein the first transmitting coil and the second transmitting coil have a resonant frequency based on an operating frequency of less than 15 MHz.

3. The system of claim 1, wherein a number of the first plurality of capacitors and a number of the second plurality of capacitors are equal.

4. The system of claim 3, wherein the first plurality of coil segments and the second plurality of coil segments each include at least four equal coil segments.

5. The system of claim 1, wherein a voltage across each of the first plurality of capacitors and the second plurality of capacitors is equal and in opposite polarity to a voltage across each of the first plurality of coil segments and the second plurality of coil segments to substantially cancel the voltage across each of the first plurality of coil segments and second plurality of coil segments.

6. The system of claim 1, wherein a value of one of the first and second plurality of capacitors is determined by:

$$f = \frac{1}{2\pi\sqrt{L_{TX}C_{TX}}};$$

where $L_{TX}$ is an inductance of the first and second transmitting coil, $C_{TX}$ is a resultant capacitance of the first and second plurality of capacitors arranged in series, and f is a resonance frequency of the wireless power transmitting device.

7. The system of claim 1, further comprising a power source coupled to the input connection and configured to deliver the excitation voltage to the input connection.

8. A system for wirelessly transferring energy to an implanted medical device, the system comprising:
a wireless power transmitting device, the wireless power transmitting device including:
a first transmitting coil having at least one conductor winding and a first radius and a first diameter;
a second transmitting coil having at least one conductor winding, a second radius, and a second diameter and arranged to extend along a common axis with the first transmitting coil, wherein the first diameter and the second diameter are substantially equal;
a gap arranged between the first transmitting coil and the second transmitting coil and extending along the common axis a distance equal to the first radius of the first transmitting coil;
a first plurality of capacitors connected in series along the at least one conductor winding of the first transmitting coil to divide the coil conductor winding into a first plurality of coil segments;
a second plurality of capacitors connected in series along the at least one conductor winding of the second transmitting coil to divide the coil conductor winding into a second plurality of coil segments; and
a power source electrically coupled to the first transmitting coil and the second transmitting coil and configured to deliver an excitation voltage to the first transmitting coil and the second transmitting coil substantially equal to a theoretical excitation voltage required to produce a substantially uniform magnetic field between the first transmitting coil and the second transmitting coil divided by a sum of the first plurality of coil segments and the second plurality of coil segments.

9. The system of claim 8, wherein the first transmitting coil and the second transmitting coil have a resonant frequency based on an operating frequency of the wireless transmission device and further comprising a wireless power receiving device, the wireless power receiving device including:
a receiving coil;
a plurality of capacitors;
the wireless power receiving device having a resonant frequency equal to the operating frequency of the wireless power transmitting device; and
wherein the wireless power receiving device is configured to convert the magnetic field generated by the wireless power transmitting device into electrical power.

10. The system of claim 8, wherein the receiving coil includes an air core.

11. A system for wirelessly transferring energy to an implanted medical device, the system comprising:
a wireless power transmitting device, the wireless power transmitting device including:
a first transmitting coil and a second transmitting coil;
the first transmitting coil and the second transmitting coil each having at least one conductor winding;
the first transmitting coil and the second transmitting coil being substantially equal in diameter;
the first transmitting coil and the second transmitting coil are located parallel to each other and separated co-axially by a distance equal to a radius of the first transmitting coil;
wherein the first transmitting coil conductor winding and the second transmitting coil conductor winding include a plurality of capacitors connected in series and further wherein the series capacitors are installed along the first transmitting coil conductor winding and the second transmitting coil conductor winding to divide the coil conductor winding into a plurality of coil segments;
the first transmitting coil and the second transmitting coil having a resonant frequency based on an operating frequency of the wireless power transmitting device; and
wherein the wireless power transmitting device is configured to produce a uniform magnetic field between the first transmitting coil and the second transmitting coil when an excitation voltage is applied to the wireless power transmitting device;
a wireless power receiving device, the wireless power receiving device including:
a receiving coil;
a plurality of capacitors;
the wireless power receiving device having a resonant frequency equal to the operating frequency of the wireless power transmitting device; and
wherein the wireless power receiving device is configured to convert the magnetic field generated by the wireless power transmitting device into electrical power.

12. The system of claim 11, wherein the first transmitting coil and the second transmitting coil have a resonant frequency based on an operating frequency of less than 15 MHz.

13. The system of claim 11, wherein a number of the first plurality of capacitors and a number of the second plurality of capacitors are equal.

14. The system of claim 13, wherein the first plurality of coil segments and the second plurality of coil segments each include at least four equal coil segments.

15. The system of claim 11, wherein a voltage across each of the first plurality of capacitors and the second plurality of capacitors is equal and in opposite polarity to a voltage across each of the first plurality of coil segments and the second plurality of coil segments to substantially cancel the voltage across each of the first plurality of coil segments and second plurality of coil segments.

16. The system of claim 11, wherein a value of one of the first and second plurality of capacitors is determined by:

$$f = \frac{1}{2\pi\sqrt{L_{TX}C_{TX}}};$$

where $L_{TX}$ is an inductance of the first and second transmitting coil, $C_{TX}$ is a resultant capacitance of the first and second plurality of capacitors arranged in series, and f is a resonance frequency of the wireless power transmitting device.

17. The system of claim 11, further comprising a power source coupled to the input connection and configured to deliver the excitation voltage to the input connection.

* * * * *